United States Patent
Koehler et al.

(10) Patent No.: US 10,568,593 B2
(45) Date of Patent: Feb. 25, 2020

(54) MULTI-FOCAL SPOT IMAGING SYSTEM

(71) Applicant: KONINKLIJKE PHILIPS N.V., Eindhoven (NL)

(72) Inventors: Thomas Koehler, Norderstedt (DE); Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 618 days.

(21) Appl. No.: 15/309,483

(22) PCT Filed: May 13, 2015

(86) PCT No.: PCT/IB2015/053530
§ 371 (c)(1),
(2) Date: Nov. 8, 2016

(87) PCT Pub. No.: WO2015/173750
PCT Pub. Date: Nov. 19, 2015

(65) Prior Publication Data
US 2017/0181716 A1   Jun. 29, 2017

Related U.S. Application Data

(60) Provisional application No. 61/993,798, filed on May 15, 2014.

(51) Int. Cl.
*A61B 6/00* (2006.01)
*A61B 6/03* (2006.01)
*A61B 6/06* (2006.01)

(52) U.S. Cl.
CPC ............ *A61B 6/4021* (2013.01); *A61B 6/032* (2013.01); *A61B 6/06* (2013.01); *A61B 6/4007* (2013.01); *A61B 6/4035* (2013.01)

(58) Field of Classification Search
CPC ......... A61B 6/032; A61B 6/06; A61B 6/4007; A61B 6/4021; A61B 6/4035
See application file for complete search history.

(56) References Cited

U.S. PATENT DOCUMENTS

2010/0166140 A1*  7/2010  Proksa ................... A61B 6/032
                                                                378/8
2010/0246756 A1*  9/2010  Forthmann ............ A61B 6/032
                                                                378/16

(Continued)

FOREIGN PATENT DOCUMENTS

| EP | 0981999 | 3/2000 |
|----|---------|--------|
| WO | 2009083850 | 7/2009 |
| WO | 2013/132361 | 9/2013 |

OTHER PUBLICATIONS

Koehler, et al., "Beam shaper with optimized dose utility for helical cone-beam CT", Med. Phys. 38 (7), Jul. 2011.

(Continued)

*Primary Examiner* — Chih-Cheng Kao
(74) *Attorney, Agent, or Firm* — Larry Liberchuk

(57) ABSTRACT

An imaging system (1400) includes a first and a second focal spot (1410$_I$ and 1410$_N$), a first pre-patient radiation beam filter (1416) disposed between the first focal spot and the examination region and having a first profile and a second pre-patient radiation beam filter (1416$_N$) disposed between the second focal spot and the examination region and having a second profile, and a source controller (1412) that controls an operation of the focal spots by modulating the operation during a scan based on at least one of an angular position of focal spots, a shape of a region of interest of subject or object being scanned, or based on a change in size between two adjacent regions of the subject or object being scanned.

19 Claims, 10 Drawing Sheets

(56) References Cited

U.S. PATENT DOCUMENTS

| | | | |
|---|---|---|---|
| 2012/0194183 A1* | 8/2012 | Shah | A61B 6/405 |
| | | | 324/309 |
| 2013/0182820 A1 | 7/2013 | Proksa | |
| 2016/0081636 A1* | 3/2016 | Kremer | A61B 6/06 |
| | | | 378/62 |

OTHER PUBLICATIONS

Forthmann, et al., "Adaptive two-pass cone-beam artifact correction using a FOV-preserving two-source gemoetry: A simulation study", Med. Phys. 36, Oct. 10, 2009.

Mail, et al., "The influence of bowtie filtration on cone-beam CT image quality", Med. Phys. 36, Jan. 2009.

\* cited by examiner

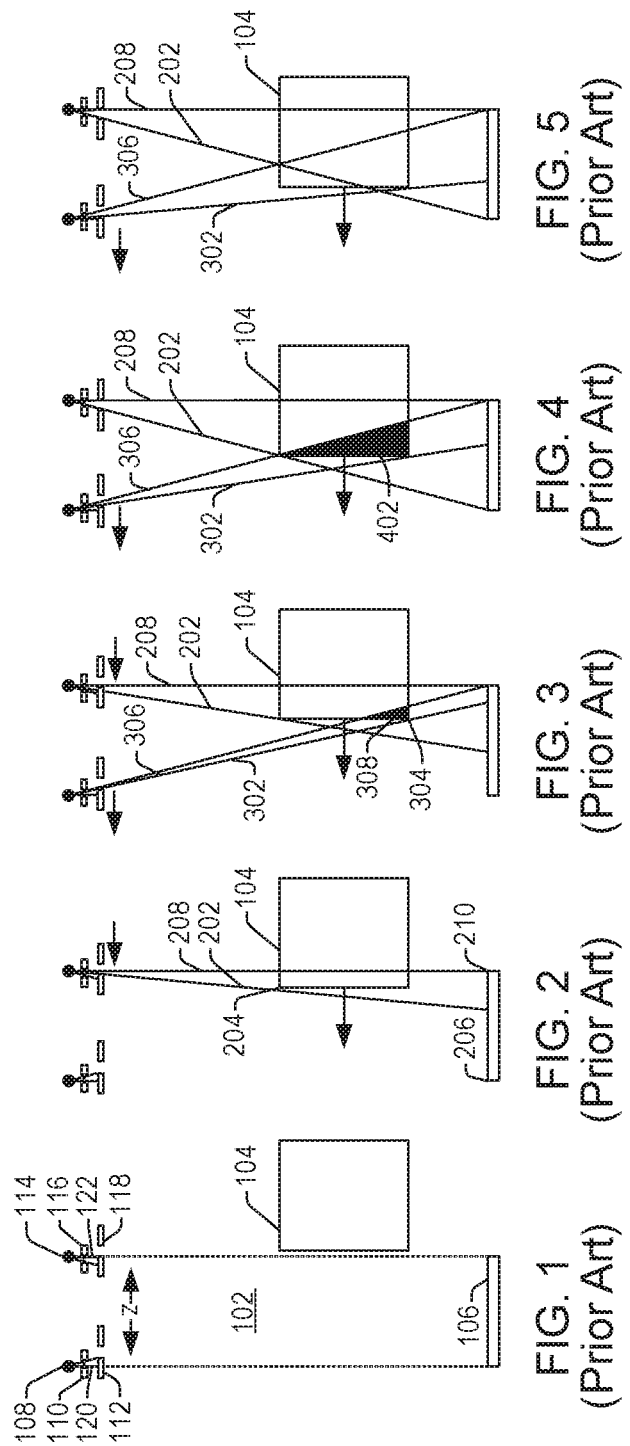

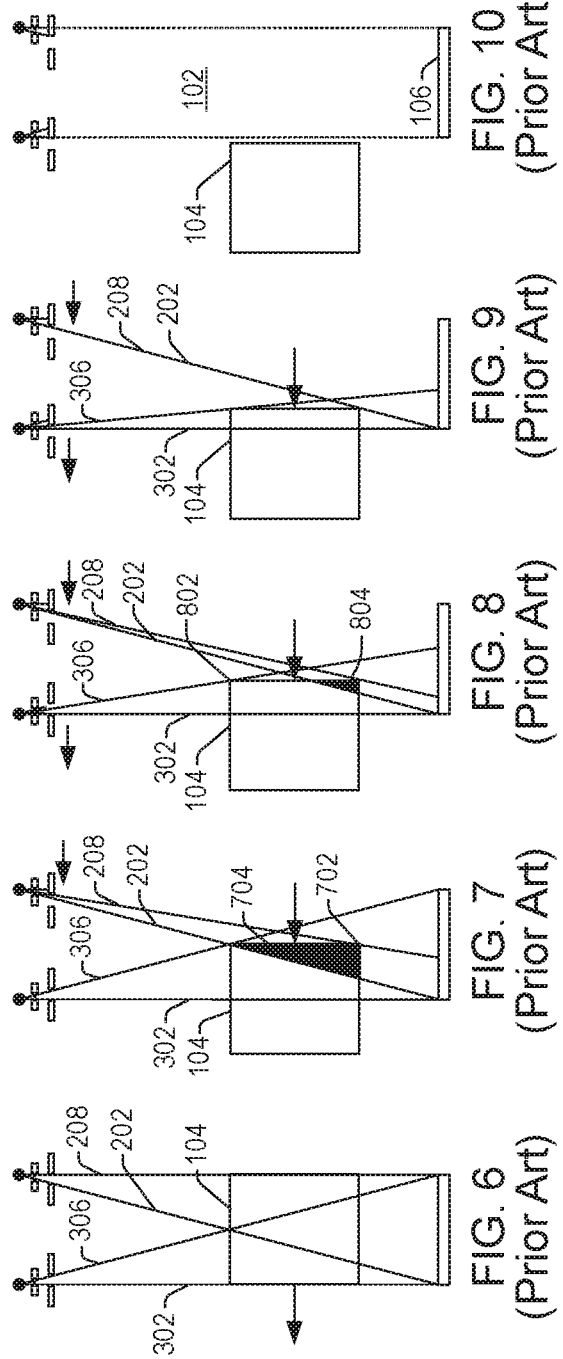

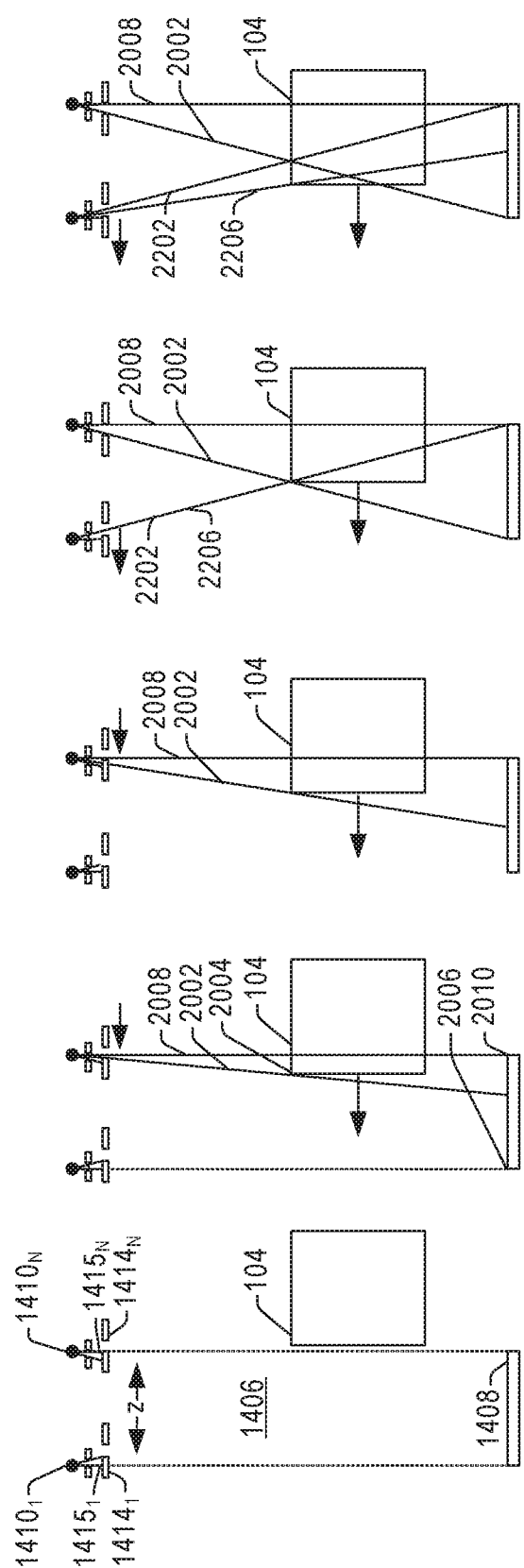

MULTI-FOCAL SPOT IMAGING SYSTEM

CROSS REFERENCE TO RELATED APPLICATIONS

This application is the U.S. National Phase application under 35 U.S.C. § 371 of International Application No. PCT/IB2015/053530, filed May 13, 2015, published as WO 2015/173750 on Nov. 19, 2015, which claims the benefit of U.S. Provisional Patent Application No. 61/993,798 filed May 15, 2014. These applications are hereby incorporated by reference herein.

The following generally relates to a multi-focal spot imaging system and is described with particular attention to a stereo tube computed tomography (CT) imaging system; however, the following is also amenable to a single x-ray tube CT imaging system with multiple focal spots.

A stereo tube computed tomography (CT) scanner includes two focal spots that alternately emit ionizing x-ray radiation that traverses an examination region and a portion of a subject or object therein. In one instance, the two focal spots respectively are part of different x-ray tubes, which are positioned at the same angle about the gantry bore, but at different z-axis locations.

A different source collimator is used with each focal spot, and a different pre-patient radiation beam filter is disposed between each focal spot and each source collimator (e.g., in the beam port of an x-ray tube). A detector array detects radiation traversing the examination region and generates projection data indicative thereof. A reconstructor reconstructs the projection data and generates volumetric image data indicative thereof.

FIG. 1 shows an example source collimator configuration in connection with an examination region 102, a reconstruction field of view (FOV) 104, and a detector array 106. A first focal spot 108 has a first static collimator 110 and a first dynamic collimator 112, and a second focal spot 114 has a second static collimator 116 and a second dynamic collimator 118. The first and second static collimators 110 and 116 collimate respective radiation beams 120 and 122 to illuminate the detector array 106.

The first and second dynamic collimators 112 and 118 provide additional collimation to limit the radiation beams 120 and 122 so that radiation traversing the examination region 102 only traverses the reconstruction FOV 104. In FIG. 1, the reconstruction FOV 104 is outside of the examination region 102, and the first and second dynamic collimators 112 and 118 are positioned so that no radiation traverses the examination region 102.

FIGS. 2-10 show how the first and second dynamic collimators 112 and 118 can be adjusted as the reconstruction FOV 104 traverses the examination region 102 so that the radiation traversing the examination region 102 only traverses the reconstruction FOV 104. FIGS. 2-10 are described in greater detail next. Certain reference numbers of FIG. 1 are left off of FIGS. 2-10 for sake of clarity.

In FIG. 2, the first dynamic collimator 112 continues to block radiation, and the second dynamic collimator 118 moves in coordination with the reconstruction FOV 104 so that an inner ray 202 of the radiation beam 122 tracks to an upper leading edge 204 of the reconstruction FOV 104 and sweeps along the detector array 106 towards an end region 206 of the detector array 106, while an outer ray 208 of the beam 122 traverses the reconstruction FOV 104 through the examination region 102 and is incident at an opposing end region 210 of the detector array 106.

In FIG. 3, the first dynamic collimator 112 moves in coordination with the reconstruction FOV 104 so that an outer ray 302 of the radiation beam 120 tracks to a lower leading edge 304 of the reconstruction FOV 104 and sweeps along the detector array 106 towards the end region 206, while an inner ray 306 of the radiation beam 122 traverses the reconstruction FOV 104 through the examination region 102 and is incident at the opposing end region 210. The second dynamic collimator 118 moves as described in FIG. 2.

In FIGS. 4 and 5, the first dynamic collimator 112 moves as described in connection with FIG. 3, and the second dynamic collimator 118 does not block any radiation from traversing the examination region 102. In FIG. 6, neither the first dynamic collimator 112 nor the second dynamic collimator 118 block any radiation from traversing the examination region 102.

In FIG. 7, the first dynamic collimator 112 does not block any radiation from traversing the examination region 102. The second dynamic collimator 118 moves in coordination with the reconstruction FOV 104 so that the outer ray 208 of the radiation beam 122 tracks to a lower trailing edge 702 of the reconstruction FOV 104 and sweeps along the detector array 106 towards the end region 206, while the inner ray 202 of the beam 122 traverses the reconstruction FOV 104 through the examination region 102 and is incident at the end region 206.

In FIGS. 8 and 9, the first dynamic collimator 112 moves in coordination with the reconstruction FOV 104 so that the inner ray 306 of the radiation beam 120 tracks to an upper trailing edge 802 of the reconstruction FOV 104 and sweeps along the detector array 106 towards the end region 206, while the outer ray 302 of the radiation beam 120 traverses the reconstruction FOV 104 through the examination region 102 and is incident at the end region 206. The second dynamic collimator 118 moves as described in FIG. 7.

In FIG. 10, the reconstruction FOV 104 moves outside of the examination region 102, and the first and second dynamic collimators 112 and 118 are positioned so that no radiation traverses the examination region 102.

The collimation configuration of FIGS. 2-10 results in homogenous image quality and noise throughout the entire reconstruction FOV 104 as all rays traversing the examination region 102 pass through the reconstruction FOV 104. However, such collimation is radiation dose inefficient. That is, regions 308, 402, 704 and 804 respectively of FIGS. 3, 4, 7 and 8 represent regions in which redundant information is collected and the subject is irradiated by both of the two focal spots 108 and 114, leading to patient dose inefficiencies.

The pre-patient radiation beam filter has been referred to as a "bowtie filter". The filter name reflects the typical shape of the filter. Theoretically, the filter has a shape that corresponds to the profile of each subject being scanned. As such, theoretically, the filter heavily attenuates regions of the beam that traverse only air, lightly attenuates the region of the beam that traverses the subject, and smoothly transitions the degree of attenuation for the transitions there between so that a correct x-ray profile can be achieved.

However, humans tend to be more elliptical in shape than cylindrical, and anterior and posterior (A/P) profiles are not the same as (i.e., are wider than) left/right side (lateral) profiles. For example, FIGS. 11 and 12 show that a pre-patient radiation beam filter 1100 with a profile that corresponds to an A/P view across the shoulders of a patient 1102 (FIG. 11) does not correspond well to a profile of the patient 1102 from shoulder to shoulder at a lateral view (FIG. 12)

as regions 1104 of the radiation beam 120, which should, theoretically, be heavily attenuated by the filter 1100, are not heavily attenuated by the filter 1100.

Furthermore, even at the same angle, the profiles of the neck and the shoulders are not the same. For example, FIGS. 11 and 13 show that the pre-patient radiation beam filter 1100 with the profile that corresponds to the A/P view across the shoulders of the patient 1102 (FIG. 11) does not correspond well to an A/P view of a head of the patient 1103 (FIG. 13). As a consequence of the above, the pre-patient radiation beam filter 1100 is not well-suited for certain angles, subjects and/or scans, and, unfortunately, may lead to an unbalanced x-ray flux and a non-homogeneous noise distribution, Aspects described herein address the above-referenced problems and others.

The following describes a multi-focal spot imaging system. In one instance, the imaging system includes multiple different sized pre-patient radiation beam filters, one pre-patient radiation beam filter for each focal spot. In this instance, the imaging system can dynamically switch between the focal spots and/or adjust the modulation of the focal spots based on a shape of the region of interest being scanned, the gantry angle, etc. In addition, the source collimation can be dynamically adjusted to improve dose efficiency by totally blocking the radiation beam from one of the focal spots to mitigate detecting redundant information.

In one aspect, an imaging system includes multi-focal spots. The imaging system further includes at least two focal spots, including at least a first focal spot and a second focal spot. The at least two focal spots are configured respectively to emit first and second radiation towards the examination region. The imaging system further includes at least two pre-patient radiation beam filters, including at least a first pre-patient radiation beam filter and a second pre-patient radiation beam filter. The first pre-patient radiation beam filter is disposed between the first focal spot and the examination region and has a first physical profile. The second pre-patient radiation beam filter is disposed between the second focal spot and the examination region and has a second physical profile. The first and the second physical profiles are different. The imaging system further includes a source controller that controls an operation of the at least two focal spots by modulating the operation of the at least two focal spots during a scan based on at least one of an angular position of the at least two focal spots, a shape of a region of interest of subject or object being scanned, or based on a change in size between two adjacent regions of the subject or object being scanned. The imaging system further includes a detector array that detects radiation traversing the examination region and generates projection data indicative thereof.

In another aspect, a method includes using a first modulation pattern to alternately operate first and second focal spots during an integration period of a scan. The first and second focal spots are arranged at about a same angular position. The method further includes using a second modulation pattern to alternately operate the first and the second focal spots during a subsequent integration period of the scan. The first and second modulation patterns are different.

In another aspect, a method includes moving a first z-axis collimator and a second z-axis collimator, wherein the first z-axis collimator is disposed between a first focal spot and an examination region and the second z-axis collimator is disposed between a second focal spot and the examination region, along a z-axis to position the first z-axis collimator and the second z-axis collimator, with respect to the first focal spot and the second focal spot, completely blocking first radiation emitted by the first focal spot from traversing an examination region and allowing second radiation emitted by the second focal spot to traverse only a reconstruction field of view traversing the examination region.

The invention may take form in various components and arrangements of components, and in various steps and arrangements of steps. The drawings are only for purposes of illustrating the preferred embodiments and are not to be construed as limiting the invention.

FIGS. 1-10 show an example of prior art stereo tube dynamic source collimation.

Figure 13:
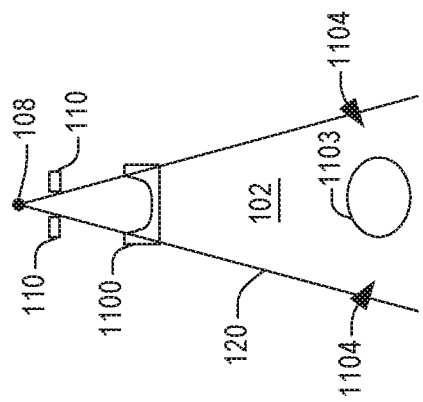
FIGS. 11-13 show an example of a prior art bowtie filter.
Figure 12:
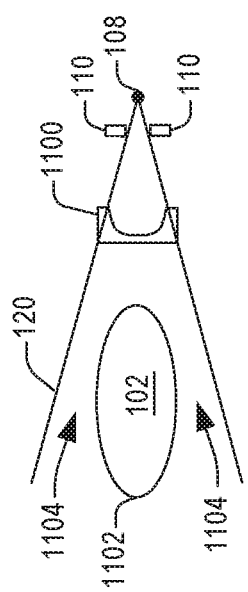
Figure 11:
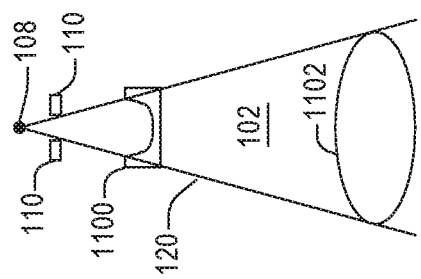
Figure 14:
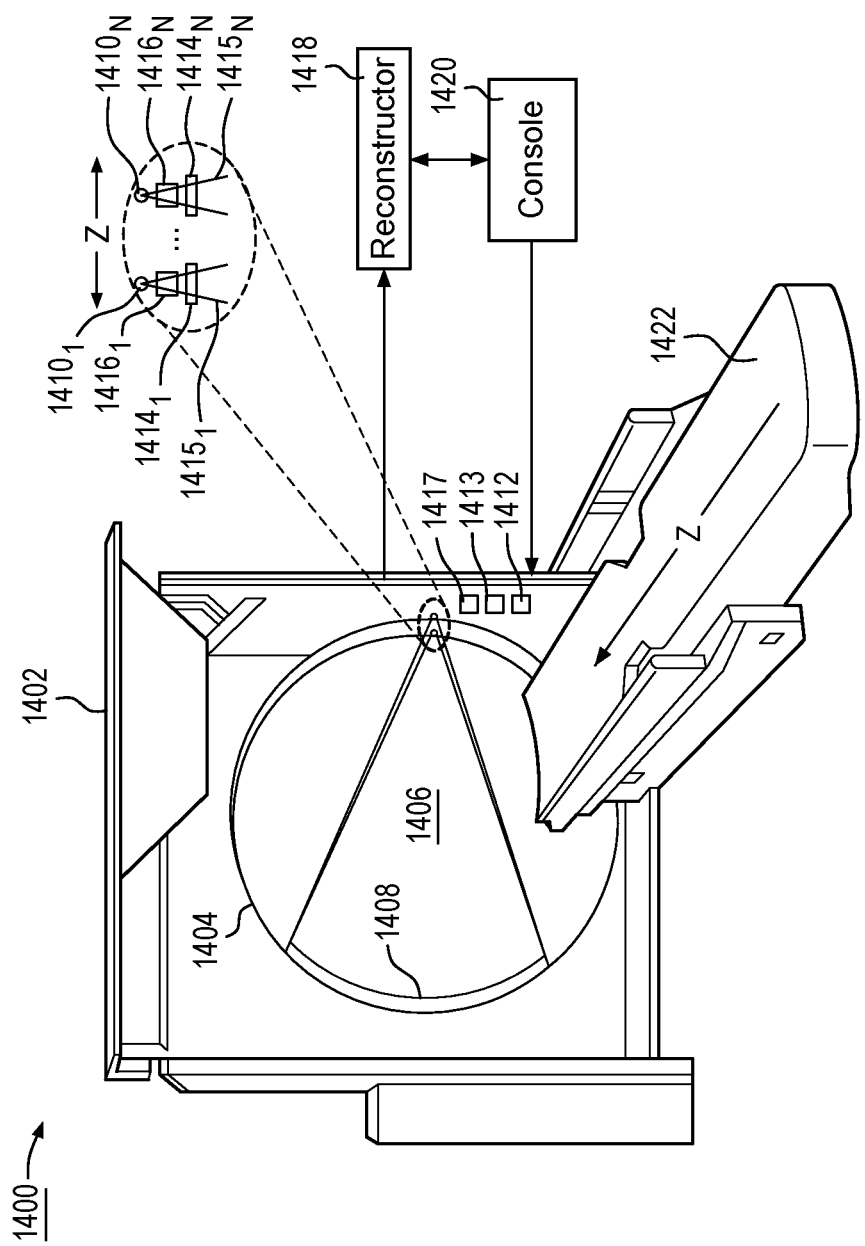

FIG. 14 schematically illustrates an example imaging system with at least two focal spots, each with a pre-patient radiation beam filter and a source collimation sub-system.

Figure 15:
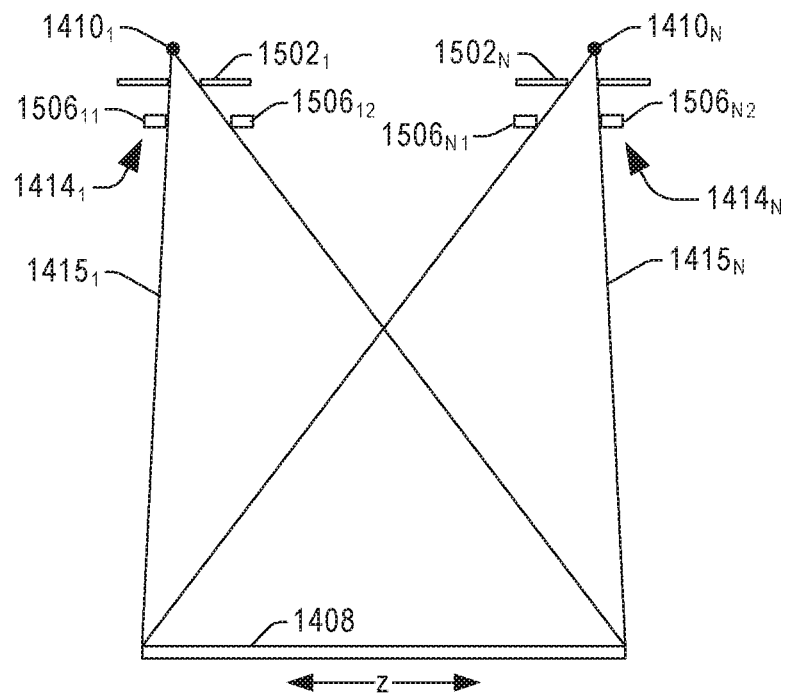

FIG. 15 schematically illustrates an example of stereo tube source collimators.

Figure 16:
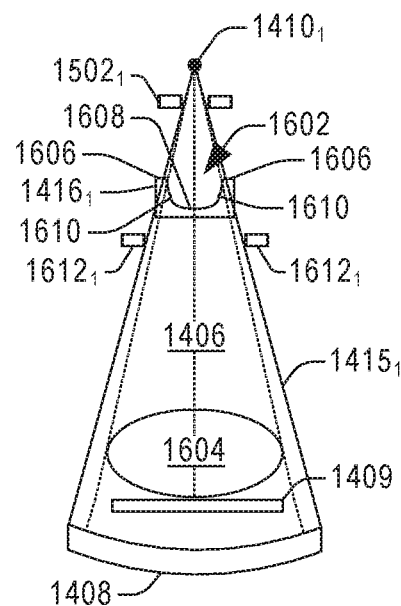

FIG. 16 schematically illustrates an example of a first of the pre-patient radiation beam filters in connection with an A/P view across the shoulders.

Figure 17:
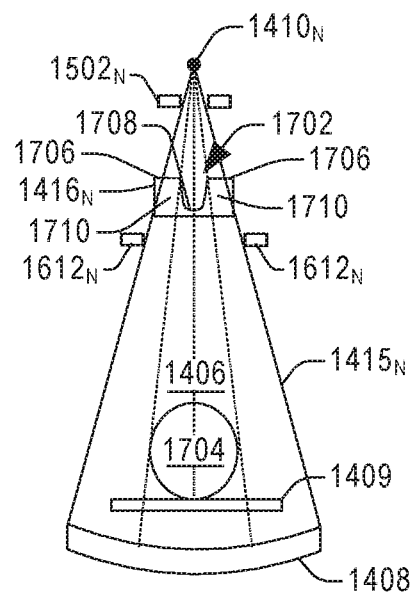

FIG. 17 schematically illustrates an example of a second of the pre-patient radiation beam filters in connection with an A/P view across the head.

Figure 18:
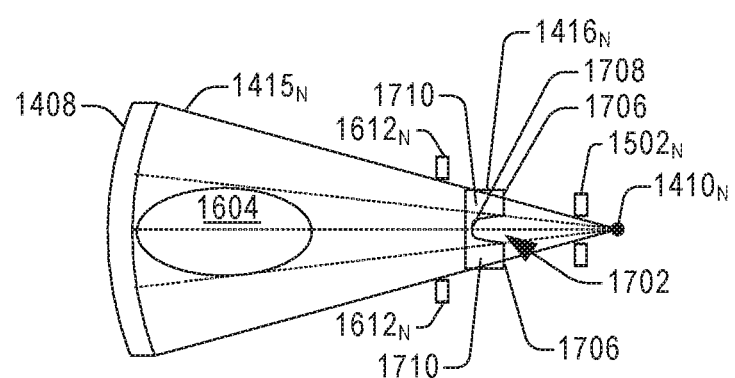

FIG. 18 schematically illustrates an example of the second of the pre-patient radiation beam filters in connection with a lateral view across the shoulders.

FIGS. 19-28 schematically illustrates example source collimation.

Figure 29:
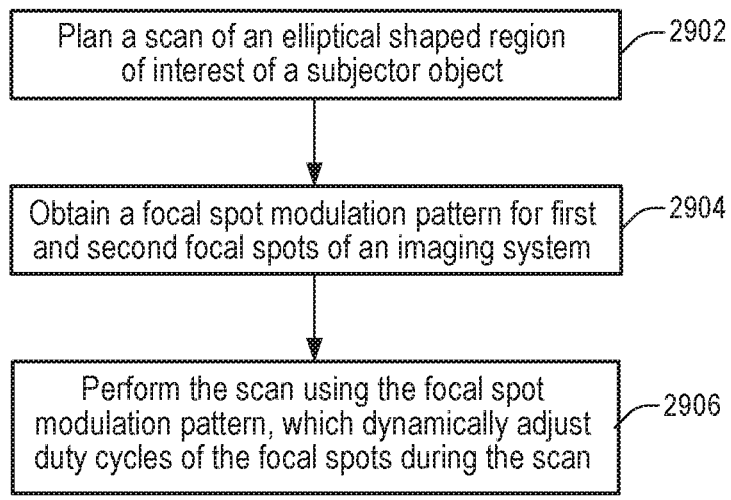
Figure 30:
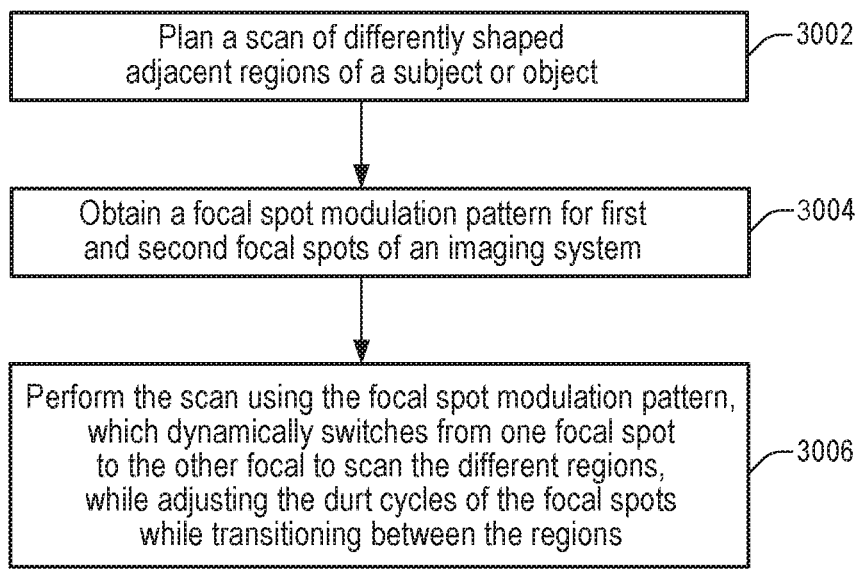
Figure 31:
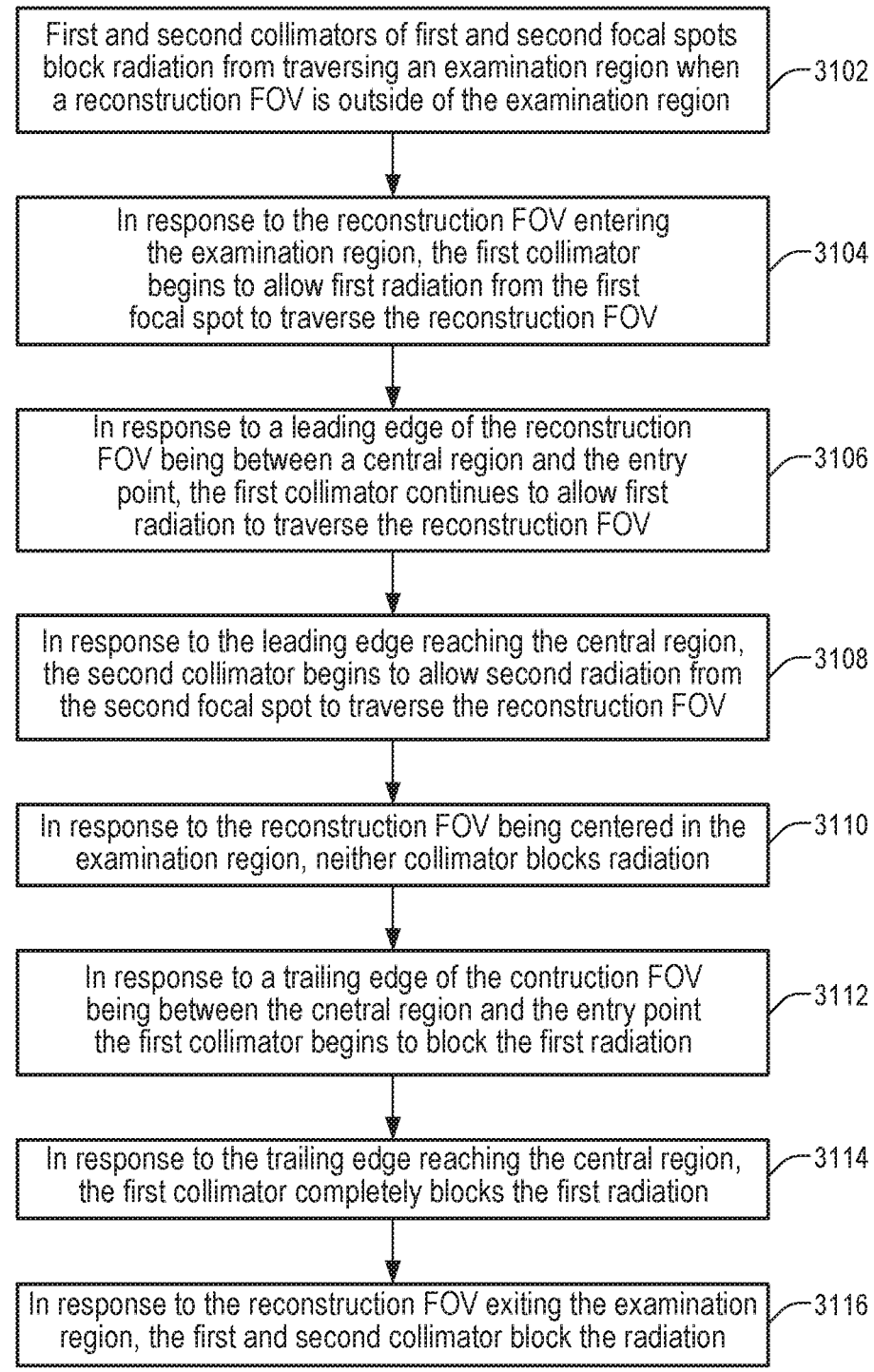

FIG. 29-31 illustrates a method for scanning with the imaging system described herein.

It is to be appreciated that the use of ordinal numbers (i.e., first, second, . . . ) in the following represents an order of introduction of the elements described herein and does not describe the elements. Thus, the terms "first" and "second" with respect to the term "focal spot" (and/or other elements) only relate to the order in which the focal spots are introduced and described herein.

Initially referring to FIG. 14, an example imaging system 1400, such as a computed tomography (CT) scanner, is schematically illustrated. The imaging system 1400 includes a generally stationary gantry 1402 and an angular rotating gantry 1404. The rotating gantry 1404 is rotatably supported by the stationary gantry 1402 and rotates around an examination region 1406 about a longitudinal or z-axis ("Z"). A one or two-dimensional radiation sensitive detector array 1408 includes a plurality of rows of detectors that extend along the z-axis direction, each row including a plurality of detector pixels. The detector array 1408 detects radiation traversing the examination region 1406 and generates projection data indicative thereof.

The illustrated imaging system 1400 includes at least two focal spots 1410$_1$, . . . , 1410$_N$ (where N is a positive integer which is larger than 1), collectively referred to herein as focal spots 1410. The focal spots 1410 are supported by and arranged on the rotating gantry 1404 at about a same angular position and offset from each other by a non-zero distance along the z-axis direction. In one instance, the focal spots 1410 are physical components of different x-ray tubes. In another instance, the focal spots 1410 are physical components of a same x-ray tube. In a configuration with three or more focal spots, the imaging system 100 may include a single x-ray tube, two x-ray tubes with one including multiple focal spots, or at least three x-ray tubes. The focal spots 1410 emit radiation that traverse the examination region 1406.

The illustrated imaging system 1400 includes a source controller 1412 that controls the focal spots 1410. The source controller 1412 is configured to turn the focal spots 1410 "on" and "off". In one instance, this includes turning the focal spots 1410 "on" and "off" so as to alternate between the focal spots 1410 so that only a single focal spot is emitting radiation at any given moment in time that traverses the examination region 1406, for example, within an integration period. In another instance, the two or more of the focal spots 1410 can be turned "on" to concurrently emit radiation. Turning a focal spot "on" and "off" can be achieved through a grid gate, a filter, and/or otherwise. The source controller 1412 can modulate the electrical current, use pulse width modulation, and/or employ another technique(s) to balance the flux incident on the detector array 1408.

A focal spot modulation pattern memory 1413 includes a plurality of different modulation patterns for the focal spots 1410. The particular modulation pattern utilized can be determined based on the selected imaging protocol, a parameter identified through a use input, a default setting, a facility setting, a pre-scan (e.g., a scout, a surview, a pilot, etc.) image, volumetric image data reconstructed during a scan, and/or otherwise. In the illustrated embodiment, the source controller 1412 controls the focal spots 1410 based on a modulation pattern from the memory 1413.

The illustrated imaging system 1400 further includes at least two z-axis source collimators $1414_1, \ldots, 1414_N$, collectively referred to herein as z-axis source collimators 1414. The at least two z-axis source collimators $1414_1, \ldots, 1414_N$ respectively are disposed between the at least two focal spots $1410_1, \ldots, 1410_N$ and the examination region 1406. The z-axis source collimators 1414 collimate the emitted x-ray radiation along the z-axis direction, producing a plurality of x-ray radiation beams $1415_1$ and $1415_N$. FIG. 15 shows an example of the z-axis source collimators 1414 in connection with the focal spots 1410. In FIG. 15, the x-ray radiation emitted by the focal spot $1410_1$ and $1410_N$ respectively passes through a first and a second set of static collimators $1502_1$ and $1502_N$.

The z-axis source collimator $1414_1$ includes at least two collimator blades $1506_{11}, \ldots, 1506_{12}$, collectively referred to herein as collimator blades 1506. The collimator blades 1506 are dynamically moveable in the z-axis direction. In one instance, the collimator blades $1506_{11}, \ldots, 1506_{12}$ collectively move together. In another instance, the collimator blades $1506_{11}, \ldots, 1506_{12}$ are individually moveable. The z-axis source collimators $1414_N$ include at least two collimator blades $1506_{N1}, 1506_{N2}$, collectively referred to herein as collimator blades 1506. The collimator blades 1506 likewise are dynamically moveable in the z-axis direction, and the collimator blades $1506_{N1}, 1506_{N2}$ are collectively or individually moveable.

Returning to FIG. 14, a source collimator controller 1417 controls the collimator blades 1506. As described in greater detail below, in one instance, the blades 1506 are controlled so that redundant information is not acquired, e.g., by totally blocking the radiation emitted by a focal spot 1410 during scanning, which may reduce overall patient dose and improve dose efficiency. In this instance, the focal spots 1410 can be employed alternately, or at least one of the focal spots 1410 can be employed continuously (e.g., at possibly reduced current), for at least for a sub-portion of a scan in which the radiation from the other focal spot is blocked (or the other focal is turned "off"). The latter allows for maintaining good angular sampling that might otherwise be degraded due to the loss of the redundant information.

With further respect to FIG. 14, the illustrated imaging system 1400 may also include at least two pre-patient radiation beam filters $1416_1, \ldots, 1416_N$, collectively referred to herein as pre-patient radiation beam filters 1416. The pre-patient radiation beam filters $1416_1, \ldots, 1416_N$ respectively are disposed between the at least two focal spots $1410_1, \ldots, 1410_N$ and the at least two source collimators $1414_1, \ldots, 1414_N$. FIG. 16 shows an example of the pre-patient radiation beam filter $1416_1$ in connection with the focal spot $1410_1$, and FIGS. 17 and 18 shows an example of the pre-patient radiation beam filter $1416_N$ in connection with the focal spot $1410_N$.

In FIG. 16, the pre-patient radiation beam filter $1416_1$ has a profile 1602 that corresponds to a general shape across shoulder and/or chest region 1604 of a typical patient. More particularly, the pre-patient radiation beam filter $1416_1$ includes first outer regions 1606 that heavily attenuates peripheral regions of the radiation that only traverse air, a central region 1608 that lightly attenuates radiation traversing the patient, and intermediate regions 1610 that smoothly transition the degree of attenuation between the regions 1606 and 1608. FIG. 16 also shows a pair x/y source collimators $1612_1$, which collimate and shape the radiation beam in the x/y direction.

In FIG. 17, the pre-patient radiation beam filter $1416_N$ has a profile 1702 that corresponds to a general shape of a head 1704 of the typical patient. More particularly, the pre-patient radiation beam filters $1416_N$ includes first out regions 1706 that heavily attenuates peripheral regions of the radiation that only traverses air, a central region 1708 that lightly attenuates radiation traversing the patient, and intermediate regions 1710 that smoothly transition the degree of attenuation between the regions 1706 and 1708. FIG. 17 also shows the pair x/y source collimators $1612_N$.

FIG. 18 shows the configuration of FIG. 17, rotated by 90 degrees, with respect to the shoulders and/or chest region 1604 of FIG. 16. In FIGS. 16, 17 and 18 the profile 1602 tracks closely to the profile of an A/P view of the shoulders and/or chest region 1604 and the profile 1702 tracks closely to the profile of the head 1704 and a lateral view of the shoulders and/or chest region 1604. However, it is to be understood that the tracking does not have to be as close as that shown. For example, the profile 1706 may be a larger or smaller for the same head 1704. Furthermore, the profile of the head 1704 and the lateral profile of the shoulders and/or chest region 1604 do not have to be the same. In general, the profiles 1602 and 1702 are different, with one more suited for wider regions and the other more suited for narrower regions.

As described in greater detail below, in one non-limiting instance, the focal spot $1410_1$ and the pre-patient radiation beam filter $1416_1$ are used for A/P shoulder and/or chest exposures (FIG. 16) and the focal spot $1410_N$ and the pre-patient radiation beam filter $1416_N$ are used for lateral shoulder and/or chest and/or head exposures (FIGS. 17 and 18). This allows for dynamic flux balancing when scanning the shoulder and/or chest and/or head regions. With protocols not using the extended coverage of the stereo tube system, the imaging system 1400 can switch between the focal spots 1410. In cases where at least two focal spots 1410 are required, for example, for extended z-axis coverage, the imaging system 1400 can change the flux by modulating the focal spots 1410 via applied electrical currents, proper pulse width, etc.

It is to be appreciated that the pre-patient radiation beam filters 1416 shown in FIGS. 16, 17 and 18 are not limiting and are provided for explanatory purposes. For example, pre-patient radiation beam filters corresponding to profiles other that at least one of the shoulders and/or check region and/or the head are also contemplated herein. In addition, there may be more than one pre-patient radiation beam filter for a particular region of the anatomy, for example, one for infants, one for adults, etc. Furthermore, the pre-patient radiation beam filters 1416 can be located at a same z-axis location and angularly offset from each other in the x-y plane, for example, in connection with a configuration in which the focal spots 1410 are located at a same z-axis location and angularly offset from each other in the x-y plane.

Referring back to FIG. 14, a reconstructor 1418 reconstructs the projection data and generates volumetric of image data indicative of the portion of the subject in the examination region. A computing system serves as an operator console 1420 and includes a human readable output device such as a monitor and an input device such as a keyboard, mouse, etc. The console 1420 allows an operator to interact with the scanner 1400 via a graphical user interface (GUI) and/or otherwise. For instance, the user can employ the input device to select an imaging protocol that selectively utilizes the different pre-patient radiation beam filters 1416 and/or selectively controls the z-axis source collimators 1506. A subject support 1422, such as a couch, supports a subject in the examination region 1406.

FIGS. 19-28 show an example dose efficient approach for collimating the radiation traversing the examination region 1406. For sake of clarity and explanatory purposes, the focal spots $1410_1, \ldots, 1410_N$, the z-axis source collimators $1414_1, \ldots, 1414_N$, the detector array 1408 and the reconstruction FOV 104 are only labeled in FIG. 19, and not in FIGS. 20-28.

In FIG. 19, the reconstruction FOV 104 is outside of the examination region 102, and the first and second dynamic collimators $1414_1, \ldots, 1414_N$ are positioned so that no radiation traverses the examination region 1406. FIGS. 20-28 show the first and second dynamic collimators $1414_1, \ldots, 1414_N$ as the reconstruction FOV 104 traverses the examination region 1406.

In FIG. 20, the first dynamic collimator $1414_1$ remains stationary. The second dynamic collimator $1414_N$ moves in coordination with the reconstruction FOV 104 so that an inner ray 2002 of the radiation beam 122 tracks to an upper leading edge 2004 of the reconstruction FOV 104 and sweeps along the detector array 1408 towards an end region 2006 of the detector array 1408, while an outer ray 2008 of the beam $1415_N$ traverses the reconstruction FOV 104 through the examination 1406 and is incident at an opposing end region 2010 of the detector array 1408.

In FIG. 21, the first dynamic collimator $1414_1$ continues to block radiation, and the second dynamic collimator $1414_N$ moves as described in connection with FIG. 20.

In FIG. 22, the first dynamic collimator $1414_1$ moves in coordination with the reconstruction FOV 104 so that an outer ray 2202 of the radiation beam $1415_1$ tracks to the leading edge 2004 of the reconstruction FOV 104 and sweeps along the detector array 1408 towards the end region 2006, while an inner ray 2206 of the beam $1415_1$ traverses the reconstruction FOV 104 through the examination 1406 and is incident at the opposing end region 2010. In FIG. 22, the outer and inner rays 2202 and 2206 overlap. The second dynamic collimator $1414_N$ does not block any radiation.

Figure 24:
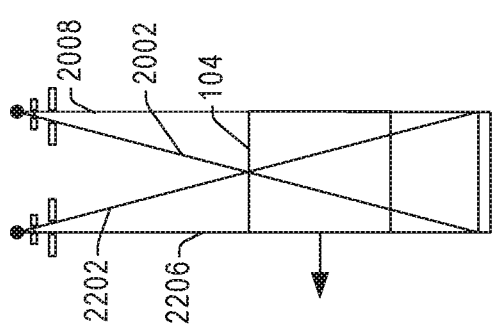

In FIG. 23, the first and second dynamic collimators $1414_1, \ldots, 1414_N$ are as described in connection with FIG. 22. In FIG. 24, neither the first nor the second dynamic collimators $1414_1, \ldots, 1414_N$ block radiation.

Figure 25:
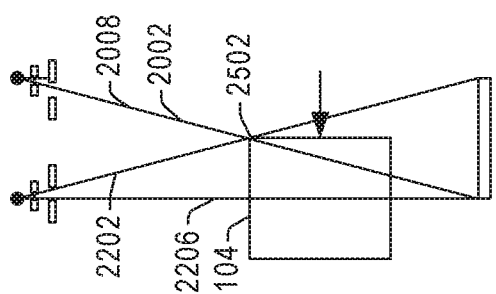

In FIG. 25, the first dynamic collimator $1414_1$ moves in coordination with the reconstruction FOV 104 so that the inner ray 2206 of the radiation beam $1415_1$ tracks to an upper trailing edge 2502 of the reconstruction FOV 104 and sweeps along the detector array 1408 towards the end region 2006, while the outer ray 2202 of the beam $1415_1$ traverses the reconstruction FOV 104 through the examination 1406 and is incident at the end region 2006 of the detector array 1408.

The second dynamic collimator $1414_N$ moves in coordination with the reconstruction FOV 104 so that the outer ray 2202 of the radiation beam $1415_N$ tracks to the upper trailing edge 2502 of the reconstruction FOV 104 and sweeps along the detector array 1408 towards the end region 2006, while the inner ray 2208 of the beam $1415_1$ traverses the reconstruction FOV 104 through the examination 1406 and is incident at the end region 2006 of the detector array 1408. In FIG. 25, the outer and inner rays 2202 and 2208 overlap.

Figure 28:
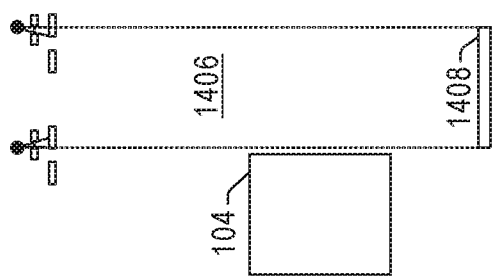
Figure 27:
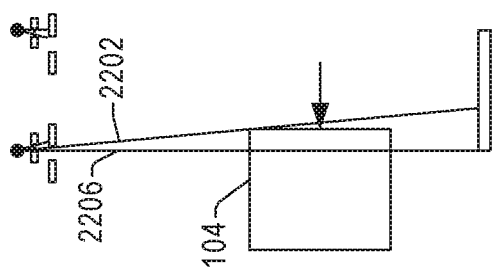
Figure 26:
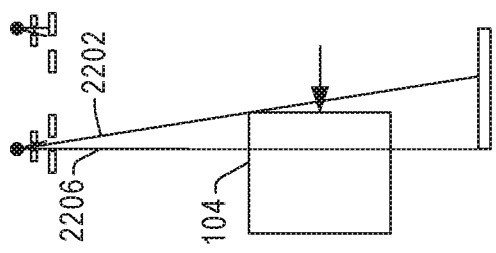

In FIG. 26, the first dynamic collimator $1414_1$ moves as described in connection with FIG. 25 and the second dynamic collimator $1414_N$ continues to block the radiation beam $1415_N$ from traversing the examination region 1406. In FIG. 27, the first and second dynamic collimators $1414_1, \ldots, 1414_N$ move as described in connection with FIG. 26. In FIG. 28, the reconstruction FOV 104 moves outside of the examination region 1406, and the first and second dynamic collimators $1414_1, \ldots, 1414_N$ are positioned so that no radiation traverses the examination region 1406.

The collimation configuration of FIGS. 19-28 improves dose efficiency relative to the configuration in FIGS. 2-10, e.g., in that the radiation beams $1415_1$ and $1415_N$ do not both traverse the regions 308, 402, 704 and 804 respectively shown in FIGS. 3, 4, 7 and 8, thereby reducing patient dose. For these regions, the focal spot $1410_N$ or $1410_1$ can be turned "on" continuously (e.g., at possibly reduced current), instead of alternately with the focal spot $1410_1$ or $1410_N$, which may maintain the same angular sampling achieved in FIGS. 3, 4, 7 and 8.

Depending on the pitch of the acquisition, further, more dose efficient collimation schemes are possible due to the increased degree of freedom with the multiple independent and dynamic collimators $1414_1, \ldots, 1414_N$.

FIGS. 29, 30, 31 illustrate example methods for scanning with the imaging system 1400.

It is to be appreciated that the ordering of the below acts is for explanatory purposes and not limiting. As such, other orderings are also contemplated herein. In addition, one or more of the acts may be omitted and/or one or more other acts may be included.

FIG. 29 illustrates a method for scanning a subject or object with a stereo tube imaging system. For explanatory purposes and sake of brevity, FIG. 29 is described in connection with an elliptical shaped region of interest of a subject or object. However, it is to be understood that one or more other non-circular shaped regions of interest and/or a circular shaped region of interest are also contemplated herein.

For this example, the imaging system has a first focal spot and a corresponding first pre-patient collimator having a first profile and a second focal spot and a corresponding second pre-patient collimator having a second profile, where the first profile is wider (or longer) than the second profile, which is narrower (or shorter).

At 2902, a scan of an elliptical shaped region of interest of the subject or object is planned. In one instance, the scan is planned using a computer based console of the imaging system.

At 2904, a focal spot modulation pattern for the elliptical shaped region of interest is obtained. In one instance, the focal spot modulation pattern is obtained from computer memory by a computer processor.

At 2906, the scan is performed using the focal spot modulation pattern, which dynamically adjusts duty cycles of the first and second focal spots during the scan depending on whether the long axis, the short axis, or a position there between is being scanned.

By way of non-limiting example, in one instance, duty cycles of 70% for the first focal spot and 30% for the second focal spot are used when the focal spots are at the 12 or 6 O'clock (or 0 or 180 degree) position, and duty cycles of 40% for the first focal spot and 60% for the second focal spot are used when the focal spots are at the 3 or 9 O'clock (or 90 or 270 degree) position. For views in between, the duty cycle dynamically changes (increases or decreases) depending on whether the focal spots 1410 are moving towards the longer axis or the shorter axis. The change in the duty cycles can be continuous or discrete.

In another example, the duty cycle for one of the focal spots can be 100%, whereas the duty cycle for the other focal spot is 0%. In another example, the duty cycle for one of the focal spots can be 50% and the duty cycle for the other focal spot is also 50%.

FIG. 30 illustrates a method for scanning a subject or object with a stereo tube imaging system.

For this example, the imaging system has a first focal spot and a corresponding first pre-patient collimator having a first profile and a second focal spot and a corresponding second pre-patient collimator having a second profile, where the first profile is wider (or longer) than the second profile, which is narrower (or shorter).

At 3002, a scan of adjacent regions of the subject or object is planned. In this example, the adjacent regions have different shapes such that one region is wider than the other region. In one instance, the focal spot modulation pattern is obtained from computer memory by a computer processor.

At 3004, a focal spot modulation pattern for the adjacent regions is obtained. In one instance, the focal spot modulation pattern is obtained from computer memory by a computer processor.

At 3006, the scan is performed using the modulation pattern, which dynamically switches the focal spot used to scan the subject or object from the first focal spot the second focal in response to transitioning from the wider region to the narrower region (or vice versa), while dynamically adjusting duty cycles of the first and second focal spots while scanning a transition region between the adjacent regions.

By way of non-limiting example, in one instance, the first focal spot and collimator are utilized to scan the shoulders/chest region. (In a variation, the method of FIG. 29 is utilized to scan this region). During the transition between the shoulders/chest region and the neck/head region, the first focal spot is utilized based on a first duty cycle and the second focal spot is utilized based on a second duty cycle. In one instance, the first duty cycle will be greater than the second duty cycle at the beginning of the transition and will dynamically change such that the second duty cycle will be greater than the first duty cycle at the end of the transition. The second focal spot and collimator are then utilized to scan the neck/head region.

FIG. 31 illustrates a method for scanning with a stereo tube imaging system.

For this example, the imaging system has a first focal spot and a corresponding first pre-patient collimator and a second focal spot and a corresponding second pre-patient collimator.

At 3102, the first collimator and the second collimator are positioned, with respect to the first focal spot and the second focal spot, to completely block first radiation emitted by the first focal spot and second radiation emitted by the second focal spot so that no radiation traverses an examination region when a reconstruction FOV is not in the examination region.

At 3104, in response to the reconstruction FOV entering the examination region, the first collimator begins to allow a sub-portion of the first radiation to traverse the examination region, but only a sub-portion of the examination region in which the reconstruction FOV is traversing, and the second collimator continues to completely block the second radiation.

At 3106, in response to an upper leading edge of the reconstruction FOV being between a central region of the examination region and the entry point, and the first collimator continues to allow a sub-portion of the first radiation to traverse the examination region, but only a sub-portion of the examination region in which the reconstruction FOV is traversing, and the second collimator continues to completely block the second radiation so that the second radiation does not traverse the examination region.

At 3108, in response to the upper leading edge of the reconstruction FOV reaching the central region of the examination region, the first collimator continues to allow a sub-portion of the first radiation to traverse the examination region, but only a sub-portion of the examination region in which the reconstruction FOV is traversing, and the second collimator begins to allow a sub-portion of the second radiation to traverse the examination region, but only a sub-portion of the examination region in which the reconstruction FOV is traversing.

At 3110, in response to the reconstruction FOV being centered at the central region of the examination region, the first collimator and the second collimator do not collimate the first radiation and the second radiation, and both the first radiation and the second radiation traverse the examination region and the reconstruction FOV traversing there through.

At 3112, in response to an upper trailing edge of the reconstruction FOV being between the central region of the examination region and the entry point, the first collimator begins to block the first radiation and allows a sub-portion of the first radiation to traverse the examination region, but only a sub-portion of the examination region in which the reconstruction FOV is traversing, and the second collimator continues to allow a sub-portion of the second radiation to traverse the examination region, but only a sub-portion of the examination region in which the reconstruction FOV is traversing.

At 3114, in response to the upper trailing edge of the reconstruction FOV reaching the central region of the examination region, the first collimator completely blocks the first radiation so that the first radiation does not traverse the examination region, and the second collimator begins to block the second radiation and allows a sub-portion of the second radiation to traverse the examination region, but only a sub-portion of the examination region in which the reconstruction FOV is traversing.

At 3116, in response to the reconstruction FOV exiting the examination region, the first collimator continues to completely block the first radiation so that the first radiation does not traverse the examination region, and the first collimator begins to completely block the radiation, and the second collimator begins to completely block the second radiation so that the second radiation does not traverse the examination region.

The above methods may be implemented by way of computer readable instructions, encoded or embedded on a computer readable storage medium, which, when executed by a computer processor(s) (e.g., a central processing unit (CPU), a microprocessor, a controller, or the like), cause the computer processor(s) to carry out the described acts. The computer readable storage medium excludes transitory medium and includes physical memory and/or other non-transitory storage medium. The computer processor(s) can also execute at least one instruction carried by a signal, carrier wave or other transitory medium, which may also cause the computer processor(s) to carry out at least one of the described acts.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A multi-focal spot computed tomography imaging system, comprising:
   at least two focal spots, including at least a first focal spot and a second focal spot, wherein the at least two focal spots are configured respectively to emit first and second radiation towards an examination region;
   at least two pre-patient radiation beam filters, including at least a first pre-patient radiation beam filter and a second pre-patient radiation beam filter, wherein the first pre-patient radiation beam filter is disposed between the first focal spot and the examination region and has a first physical profile, and the second pre-patient radiation beam filter is disposed between the second focal spot and the examination region and has a second physical profile, wherein the first and the second physical profiles are different;
   a source controller configured to control an operation of the at least two focal spots by modulating the operation of the at least two focal spots during a scan based on at least one of an angular position of the at least two focal spots, a shape of a region of interest of a subject or object being scanned, or based on a change in size between two adjacent regions of the subject or object being scanned;
   a detector array configured to detect radiation traversing the examination region and generate projection data indicative thereof;
   at least two z-axis source collimators, including a first z-axis collimator and a second z-axis collimator, wherein the first z-axis collimator is disposed between the first focal spot and the examination region and the second z-axis collimator is disposed between the second focal spot and the examination region; and
   a collimator controller configured to independently control the at least two z-axis source collimators so as to collimate the first and second radiation so that redundant information is not acquired by the detector array.

2. The imaging system of claim 1, wherein the first focal spot and the second focal spot are arranged at about a same angular position about an examination region of the imaging system and offset from each other by a non-zero distance along a z-axis direction.

3. The imaging system of claim 1, further comprising:
   at least two x-ray tubes, wherein each of the at least two x-ray tubes includes one of the at least two focal spots.

4. The imaging system of claim 1, further comprising:
   a single x-ray tube that includes the at least two focal spots.

5. The imaging system of claim 1, wherein the source controller is configured to employ only one of the at least two focal spots at a first angular position during the scan and only a different one of the at least two focal spots at a second different angular position during the scan.

6. The imaging system of claim 1, wherein the source controller is configured to alternately employ the at least two focal spots at a first angular position.

7. The imaging system of claim 6, wherein the source controller is configured to use a same first duty cycle for each of the at least two focal spots.

8. The imaging system of claim 6, wherein the source controller is configured to use a first duty cycle for the first focal spot and a second duty cycle for the second focal spot, wherein the first and the second duty cycles are different.

9. The imaging system of claim 8, wherein the source controller is configured to alternately employ the at least two focal spots at a second different angular position, wherein the source controller is configured to use a third duty cycle for the first focal spot and a fourth duty cycle for the second focal spot, wherein the first and third duty cycles are different and the second and fourth duty cycles are different.

10. The imaging system of claim 9, wherein the collimator controller is configured to control the at least two z-axis source collimators so that one of the at least two z-axis source collimators completely blocks radiation from traversing the examination region and a different one of the at least two z-axis collimators allows radiation to traverse the examination region, in response to a reconstruction field of view traversing the examination region.

11. The imaging system of claim 1, wherein the source controller is configured to continuously employ the z-axis collimator allowing radiation to traverse the examination region so that it allows radiation to traverse the examination region while the one of the at least two z-axis source collimators completely blocks the radiation from traversing the examination region.

12. The imaging system of claim 1, wherein the collimator controller is configured to transition the z-axis collimator allowing radiation to traverse the examination region so that it completely blocks radiation from traversing the examination region and to transition the z-axis collimator blocking radiation from traversing the examination region so that it allows radiation to traverse the examination region, in response to the reconstruction field of view traversing the examination region.

13. A tomography imaging method, comprising:
   moving a first z-axis collimator and a second z-axis collimator along a z-axis, wherein the first z-axis collimator is disposed between a first focal spot and an examination region and the second z-axis collimator is disposed between a second focal spot and the examination region; and
   positioning the first z-axis collimator and the second z-axis collimator, with respect to the first focal spot and the second focal spot, so as to completely block first radiation emitted by the first focal spot from traversing an examination region and to allow second radiation emitted by the second focal spot to traverse only a reconstruction field of view traversing the examination region.

14. The method of claim 13, further comprising:
   using a first modulation pattern to alternately operate first and second focal spots during an integration period of a scan; and using a second modulation pattern to alternately operate the first and the second focal spots during a subsequent integration period of the scan, wherein the first and second modulation patterns are different.

15. The method of claim 14, wherein the first and second modulation patterns identify a duty cycle for each of the first and second focal spots for each of the integration period and the subsequent integration period, wherein the duty cycle for the first focal spot and the duty cycle for the second focal spot are different between the integration period and the subsequent integration period.

16. The method of claim 14, wherein the integration period and the subsequent integration period occur at a same angular position for different regions of interest of a subject or object.

17. The method of claim 14, wherein the integration period and the subsequent integration period occur at different angular positions for a same region of interest of a subject or object.

18. The method of claim 14, wherein the first and second focal spots are arranged at about a same angular position and offset from each other by a non-zero distance along a z-axis direction.

19. The method of claim 13, further comprising, at least one of:

moving the first z-axis collimator and the second z-axis collimator along the z-axis to position the first z-axis collimator and the second z-axis collimator, with respect to the first focal spot and the second focal spot, so as to allow the first radiation to traverse only the reconstruction field of view traversing the examination region and to completely block the second radiation from traversing the examination region; or alternating the focal spots to emit radiation in response to the first and second z-axis collimators so as to allow the first and the second radiation to traverse only the reconstruction field of view traversing the examination region; and continuously employing only the focal spot emitting radiation that traverses the reconstruction field of view traversing the examination region in response to the other focal spot not emitting radiation that traverses the examination region.

\* \* \* \* \*